United States Patent
Ikeda et al.

(10) Patent No.: US 9,204,810 B2
(45) Date of Patent: Dec. 8, 2015

(54) BLOOD PRESSURE METER

(71) Applicant: OMRON HEALTHCARE Co., Ltd., Kyoto (JP)

(72) Inventors: Keita Ikeda, Kyoto (JP); Masataka Yanagase, Kyoto (JP); Shingo Yamashita, Kyoto (JP); Takanori Nishioka, Kyoto (JP); Izumi Hachimaru, Tokyo (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 14/390,075

(22) PCT Filed: Apr. 3, 2013

(86) PCT No.: PCT/JP2013/060225
§ 371 (c)(1),
(2) Date: Oct. 2, 2014

(87) PCT Pub. No.: WO2013/151099
PCT Pub. Date: Oct. 10, 2013

(65) Prior Publication Data
US 2015/0112213 A1    Apr. 23, 2015

(30) Foreign Application Priority Data

Apr. 5, 2012 (JP) ................. 2012-086233

(51) Int. Cl.
*A61B 5/02* (2006.01)
*A61B 5/022* (2006.01)
(Continued)

(52) U.S. Cl.
CPC ............ *A61B 5/02233* (2013.01); *A61B 5/021* (2013.01); *A61B 5/02255* (2013.01);
(Continued)

(58) Field of Classification Search
CPC ...... A61B 5/02; A61B 5/02422; A61B 5/021; A61B 5/022; A61B 5/02233; G02F 1/133603
See application file for complete search history.

(56) References Cited

U.S. PATENT DOCUMENTS

| 2004/0027510 A1* | 2/2004 | Iijima et al. ............... 349/61 |
| 2010/0249658 A1* | 9/2010 | Sherman et al. ............ 600/587 |
| 2011/0237963 A1* | 9/2011 | Nishioka et al. ............ 600/493 |

FOREIGN PATENT DOCUMENTS

| JP | 2011-139829 A | 7/2011 |
| WO | 2010/067723 A1 | 6/2010 |
| WO | 2010/071044 A1 | 6/2010 |

OTHER PUBLICATIONS

International Search Report for corresponding International Application No. PCT/JP2013/060225, mailed May 7, 2013 (1 page).

(Continued)

*Primary Examiner* — Jacqueline Cheng
*Assistant Examiner* — Puya Agahi
(74) *Attorney, Agent, or Firm* — Osha Liang LLP

(57) ABSTRACT

A blood pressure meter includes a cuff serving as a blood pressure measurement cuff, a main body attached in an opposing manner to the cuff, a display unit having a rectangular width and being arranged along an external face of the main body on a side opposite to the cuff, and first to third light emitting elements serving as light emitting units arranged inside the main body at positions that are farther from the external face than the display unit is. The first to third light emitting elements serving as a light emitting unit are arranged in a row in the width direction of the cuff. The display unit has a cutout portion at the center of one end side with respect to the direction in which the cuff extends. The cutout portion is formed by cutting out a region corresponding to the first to third light emitting elements.

8 Claims, 6 Drawing Sheets

(51) Int. Cl.
  *A61B 5/0225* (2006.01)
  *A61B 5/00* (2006.01)
  *A61B 5/021* (2006.01)
  *G02B 5/30* (2006.01)
  *G02F 1/1335* (2006.01)

(52) U.S. Cl.
  CPC .............. *A61B5/6824* (2013.01); *A61B 5/742* (2013.01); *G02B 5/3083* (2013.01); *G02F 1/133528* (2013.01); *G02F 1/133553* (2013.01); *G02F 1/133603* (2013.01)

(56) References Cited

OTHER PUBLICATIONS

Written Opinion for corresponding International Application No. PCT/JP2013/060225, mailed May 7, 2013 (6 pages).

* cited by examiner

BLOOD PRESSURE METER

TECHNICAL FIELD

The present invention relates to a blood pressure meter including a liquid crystal display unit.

BACKGROUND ART

JP 2011-139829A (Patent Literature 1) discloses an example of a type of conventional blood pressure meter. This blood pressure meter includes a main body, a segment liquid crystal panel provided on the surface of the main body, and an LED provided on the surface of the main body in a region different from that of the segment liquid crystal panel. Also, the segment liquid crystal panel displays information related to the blood pressure of a measurement subject. Also, the LED displays orientation information indicating the orientation of the measurement subject at the time of measuring blood pressure.

CITATION LIST

Patent Literature

Patent Literature 1: JP 2011-139829A

SUMMARY OF INVENTION

Technical Problem

However, with the conventional blood pressure meter described above, since the LED is arranged on the surface of the main body in a region different from that of the segment liquid crystal panel, there is a problem in that the main body of the blood pressure meter is larger and it is difficult to achieve a reduction in size.

Also, for example, if a semi-transmissive type of liquid crystal panel is used instead of the segment liquid crystal panel, the LED can be placed at a position overlapping the liquid crystal panel in a view from the front, which makes it possible to realize a reduction in the product size. However, light emitted from the LED that has passed through the semi-transmissive liquid crystal panel will not be clear. For this reason, there is a problem in that the orientation information of the measurement subject at the time of blood pressure measurement cannot be indicated clearly by the LED, which reduces usability.

In view of this, it is an object of the present invention to provide a blood pressure meter by which a reduction in product size can be achieved without reducing usability.

Solution to Problem

In order to solve the above-described problem, a blood pressure meter according to the present invention includes:

a blood pressure measurement cuff configured to be wrapped around a measurement site;

a main body attached in an opposing manner to the blood pressure measurement cuff;

a display unit arranged extending along an external face of the main body on the side opposite to the blood pressure measurement cuff and configured to display information related to the blood pressure of a measurement subject; and a light emitting unit arranged inside of the main body at a position that is farther from the external face than the display unit is, wherein the display unit includes a reflecting plate, a first polarizing plate, a liquid crystal display element, and a second polarizing plate in the stated order in a first direction from the inside to the external face of the main body, and regions of the reflecting plate and the first polarizing plate that correspond to the light emitting unit are cut out such that light from the light emitting unit is emitted through the liquid crystal display element and the second polarizing plate along the first direction.

In the present specification, "information related to blood pressure" refers generally to systolic blood pressure (SBP), which is the maximum blood pressure, diastolic blood pressure, which is the minimum blood pressure, pulse rate, and the like.

With the blood pressure meter of the present invention, the reflecting plate and the first polarizing plate of the display unit have regions cut out that correspond to the light emitting unit, and light from the light emitting unit is emitted along the first direction through the liquid crystal display element and the second polarizing plate. For this reason, the light emitting unit can be arranged so as to overlap with the display unit with respect to the first direction, and therefore the area of the main body can be reduced with respect to the direction that is orthogonal to the first direction and a reduction in the size of the blood pressure meter can be realized. Also, light that has been emitted from the light emitting unit through the liquid crystal display element and the second polarizing plate is clearer than light that has been emitted through a semi-transmissive type of liquid crystal panel, for example. In view of this, if the orientation information of the measurement subject at the time of blood pressure measurement is indicated by the light emitting unit, the orientation information of the measurement subject can be clearly indicated. Accordingly, with the blood pressure meter, it is possible to achieve a reduction in the product size without reducing usability.

With the blood pressure meter according to an embodiment, the main body includes:

an angle detection unit configured to detect an angle of the measurement site with respect to a pre-determined reference angle; and a light emission control unit configured to perform control for causing the light emitting unit to emit light based on the angle detected by the angle detection unit.

With the blood pressure meter of the embodiment, the light emitting unit emits light based on an angle detect by the angle detection unit. For this reason, the angle of the measurement site, or in other words, the orientation information of the measurement subject, at the time of blood pressure measurement can be indicated clearly using the light emitting unit. Accordingly, the measurement subject can measure his or her blood pressure at the correct orientation based on the orientation information.

With the blood pressure meter according to an embodiment, the light emitting unit includes three light emitting elements arranged in a row along a width direction of the blood pressure measurement cuff, and the light emission control unit causes a first light emitting element arranged in the center of the three light emitting elements to emit light when the detected angle is within a pre-determined range, the light emission control unit causes a second light emitting element arranged on one side of the three light emitting elements to emit light when the detected angle is larger than a pre-determined range, and the light emission control unit causes a third light emitting element arranged on the other side of the three light emitting elements to emit light when the detected angle is smaller than a pre-determined range.

With the blood pressure meter according to the embodiment, the first light emitting element emits light when the detected angle is within a pre-determined range, the second light emitting element emits light when the detected angle is larger than a pre-determined range, and the third light emitting element emits light when the detected angle is smaller than a pre-determined range. For this reason, it is possible to indicate the orientation information of the measurement subject more clearly according to which of the first to third light emitting elements is emitting light. Accordingly, the measurement subject can measure his or her blood pressure with greater accuracy at the correct orientation based on the orientation information.

With the blood pressure meter according to an embodiment, a color of light emitted by the first light emitting element and a color of light emitted by the second and third light emitting elements are different.

With the blood pressure meter according to an embodiment, a color of light emitted by the first light emitting element and a color of light emitted by the second and third light emitting elements are different, and therefore the orientation information of the measurement subject can be indicated more clearly by the first to third light emitting elements. Accordingly, the measurement subject can measure his or her blood pressure with greater accuracy at the correct orientation based on the orientation information.

With the blood pressure meter according to an embodiment, the main body includes a partition portion that partitions light emitted by the three light emitting elements respectively.

With the blood pressure meter according to the embodiment, light emitted by the three light emitting elements respectively is partitioned by the partition portion, and therefore it is easier for the measurement subject to see which of the light emitting elements is emitting light. Accordingly, the orientation information of the measurement subject can be indicated more clearly, and the measurement subject can measure his or her blood pressure with greater accuracy at the correct orientation based on the orientation information.

With the blood pressure meter according to an embodiment, between the reflecting plate and the three light emitting elements, the main body includes a holder having a planar dimension that is substantially the same as the planar dimension of the liquid crystal display element, in regions that correspond to the three light emitting elements with respect to a direction orthogonal to the first direction, the holder includes a light emission path that allows light from the light emitting element to pass in the first direction, and the partition portion is formed in regions of the holder that are between adjacent light emission paths.

With the blood pressure meter according to the embodiment, the partition portion is formed at a portion of the holder that is between adjacent light emission paths. Accordingly, light emitted from the three light emitting elements can be partitioned using a simple construction without providing an additional partition portion.

With the blood pressure meter according to an embodiment, the holder has a thickness that exceeds the dimension of the light emitting element with respect to the first direction, and the dimension in a direction orthogonal to the first direction of the light emission path increases with respect to the first direction.

With the blood pressure meter according to the embodiment, the dimension in the direction orthogonal to the first direction of the light emission path increases in the first direction. Accordingly, compared to the case where the dimension of the light emission path in the direction orthogonal to the first direction is constant along the first direction, the range of light emitted from the light emitting element is wider and it is easier for the measurement subject to see the light from the light emitting element.

Advantageous Effects of Invention

As can be understood from the description above, the blood pressure meter of the present invention can achieve a reduction in product size without reducing usability.

DESCRIPTION OF EMBODIMENTS

Hereinafter, an embodiment of the invention will be described in detail with reference to the drawings.

Figure 1:
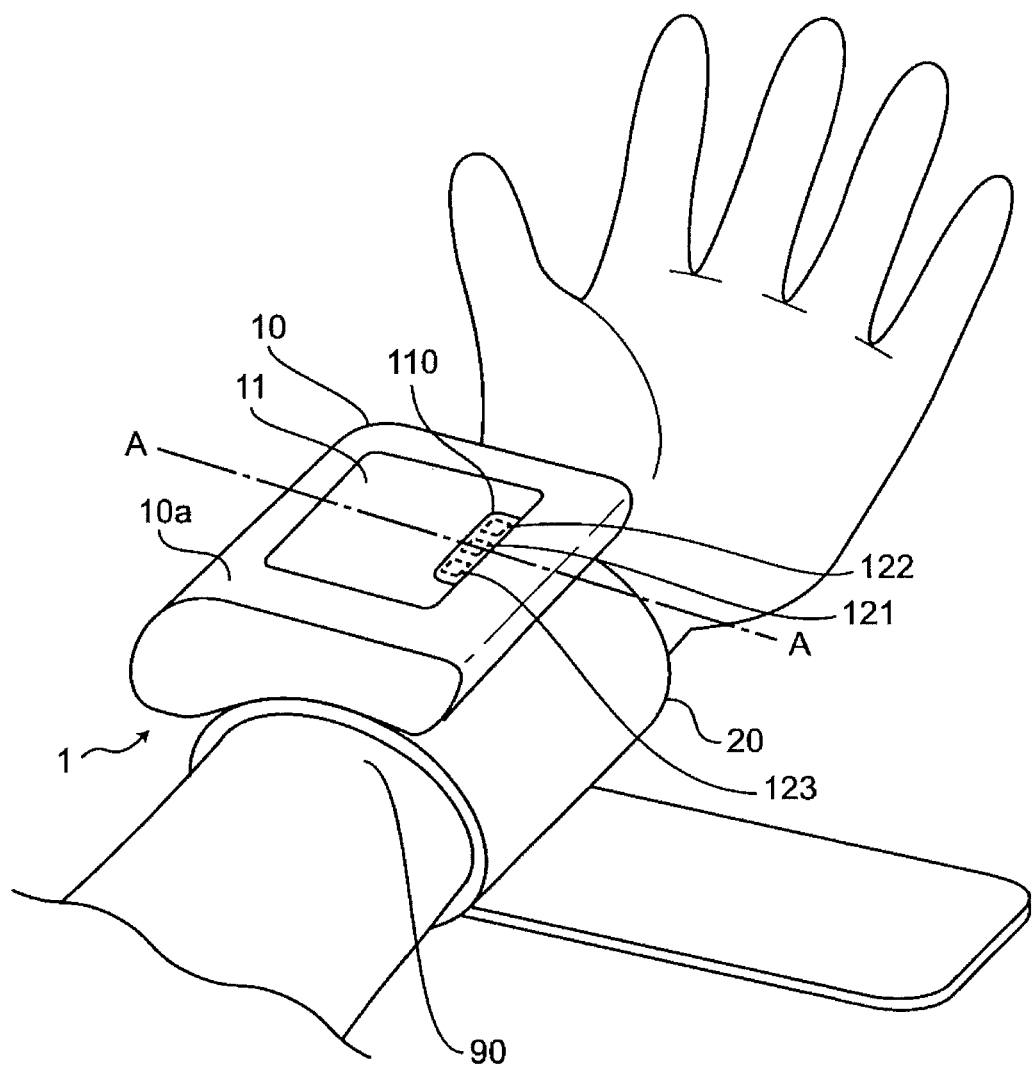
FIG. 1 is a perspective view showing the external appearance of a blood pressure meter of the present invention when attached to a wrist of a measurement subject.

FIG. 1 shows an attached state in which a blood pressure meter (indicated as a whole by the reference numeral "1") according to an embodiment of the invention is attached to a left wrist 90 serving as a measurement site of a measurement subject.

As shown in FIG. 1, the blood pressure meter 1 of the embodiment includes a cuff 20 serving as a blood pressure measurement cuff, and a main body 10 that is attached in an opposing manner to the cuff 20. Also, the blood pressure meter 1 includes a display unit 11 that is arranged along an external face 10a that is on the side of the main body 10 that is opposite to the cuff 20, and first to third light emitting elements 121 to 123 serving as light emitting units arranged inside the main body 10 at a position that is farther from the outer face 10a than the display unit 11 is.

The cuff 20 is composed of a belt-shaped cloth bladder. When wrapped around the left wrist 90, the cuff 20 has an external circumferential portion that is located on the external circumferential side, and an internal circumferential portion that is located on the internal circumferential side. A surface fastener (not shown) is provided on a portion of the external circumferential portion and a portion of the internal circumferential portion of the cuff 20. The blood pressure meter 1 is attached by wrapping the cuff 20 around the left wrist 90. In the attached state, the blood pressure meter 1 is fixed and held to the left wrist 90 by the surface fastener such that the external face 10a of the main body 10 faces the same direction as the palm of the left hand.

The display unit 11 is roughly rectangular in shape. Information related to the blood pressure of the measurement subject, such as SBP, DBP and pulse rate, are displayed on the display unit 11. The first to third light emitting elements 121 to 123 of the light emitting unit are arranged in a row along the width direction of the cuff 20 in the following order from the upper arm side to the hand side: third light emitting element 123, first light emitting element 121, and second light emitting element 122. Also, the first to third light emitting elements 121 to 123 are the same size and are arranged at an equal interval. The first to third light emitting elements 121 to 123 display information indicating the angle of the left wrist 90 (this will be described in detail later).

Figure 2:
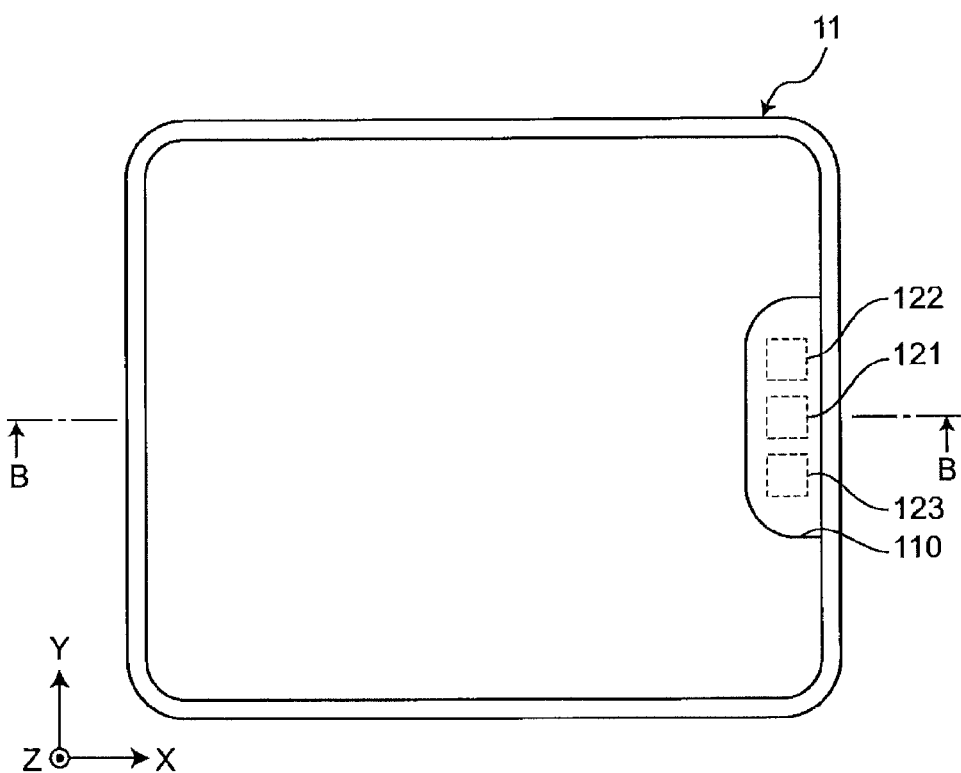
FIG. 2 is a plan view showing a display unit of the blood pressure meter.
Figure 3:
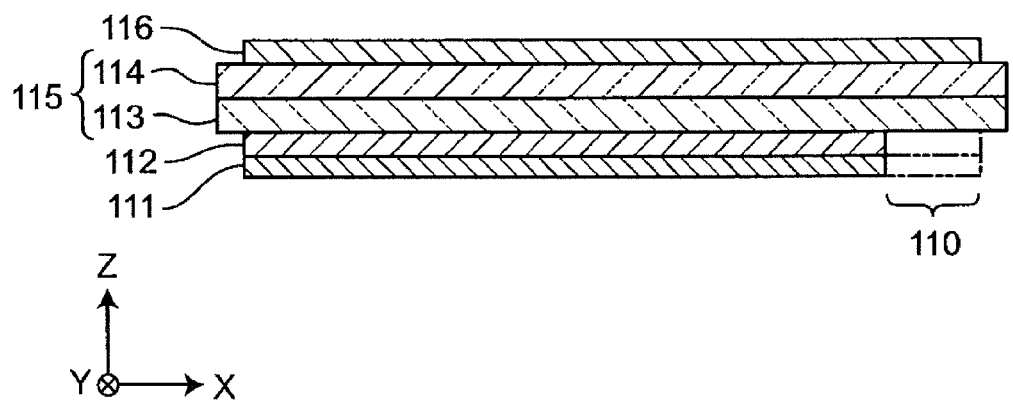
FIG. 3 is a diagram showing a cross section of the display unit taken along line B-B in FIG. 2.

FIG. 2 shows the display unit 11 as viewed from the front. Also, FIG. 3 shows a cross section of the display unit 11 taken along line B-B in FIG. 2. Note that in FIGS. 2 and 3, orthogonal coordinates X, Y, and Z are provided to facilitate understanding (the same goes for FIGS. 4 and 5 as well).

As shown in FIG. 2, a roughly rectangular cutout portion 110 is provided on the display unit 11 in correspondence with the first to third light emitting elements 121 to 123.

As shown in FIG. 3, the display unit includes a reflecting plate 111, a first polarizing plate 112, a lower glass 113, an upper glass 114, and a second polarizing plate 116 in the stated order in a first direction from the interior to the external face 10a of the main body 10, or in other words, in the Z direction from the lower side to the upper side in FIG. 2.

The cutout portion 110 is formed by cutting out a region of the reflecting plate 111 and the first polarizing plate 112 of the display unit 11 that corresponds to the first to third light emitting elements 121 to 123.

The lower glass 113 and the upper glass 114 are constituted by a transparent glass base material. Also, a liquid crystal layer (not shown) is provided between the lower glass 113 and the upper glass 114, and the liquid crystal layer, the lower glass 113, and the upper glass 114 form a liquid crystal display element 115.

The reflecting plate 111 reflects light that is received from the external face 10a of the main body 10 and has reached the reflecting plate 111 through the second polarizing plate 116, the liquid crystal display element 115, and the first polarizing plate 112.

Figure 4:
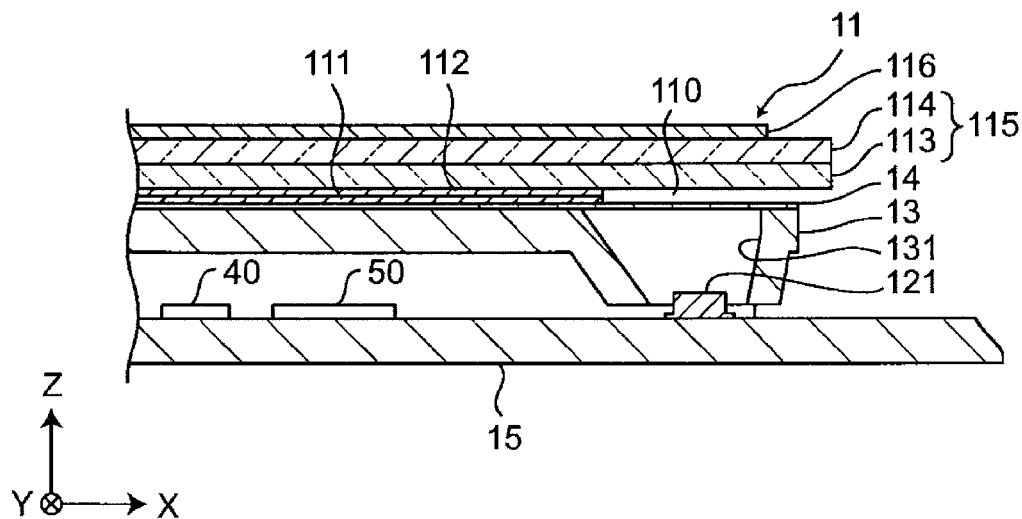
FIG. 4 is a diagram showing a partial cross-section of a main body of the blood pressure meter taken along line A-A in FIG. 1.

FIG. 4 shows a partial cross section of the main body 10 taken along line A-A in FIG. 1. Specifically, a cross section of parts including the display unit 11 and the first to third light emitting elements 121 to 123 arranged inside of the main body 10 is shown.

The first to third light emitting elements 121 to 123 are arranged on a substrate 15 provided inside of the main body 10. Specifically, the first to third light emitting elements 121 to 123 are constituted by light emitting diodes, planar light emitting lasers, or the like. The color of light emitted by the first light emitting element 121 is blue, and the color of light emitted by the second and third light emitting elements 122 and 123 is orange.

A holder 13 constituted by a rectangular plate-shaped member holding the liquid crystal display element 115 is arranged between the first to third light emitting elements 121 to 123 and the liquid crystal display element 115. The holder 13 extends parallel to the liquid crystal display element 115 and has a planar dimension that is substantially the same as the planar dimension of the liquid crystal display element in the XY plane.

Figure 5:
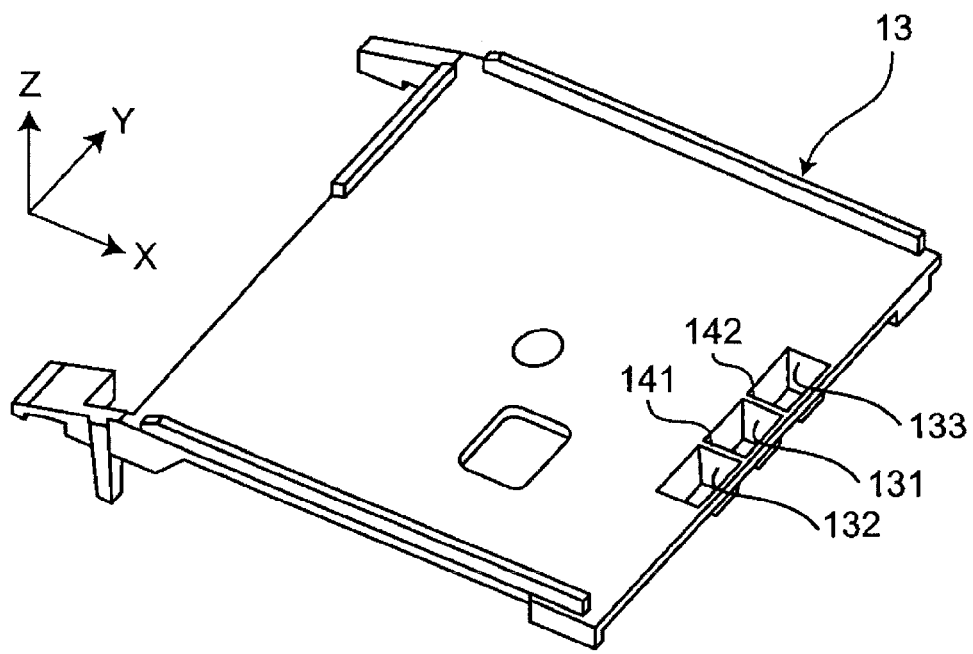
FIG. 5 is a perspective view showing the external appearance of a holder for the blood pressure meter.

As shown in FIG. 5, the holder 13 has first to third holes 131 to 133 serving as light emission paths at positions corresponding to the first to third light emitting elements 121 to 123. The first to third holes 131 to 133 have the same size and shape. A first partition portion 141 that partitions light emitted from the first light emitting element 121 and light emitted from the second light emitting element 122 is formed at the portion of the holder 13 that is between the first hole 131 and the second hole 132. Also, a second partition portion 142 that partitions light emitted from the first light emitting element 121 and light emitted from the third light emitting element 123 is formed at the portion of the holder 13 that is between the first hole 131 and the third hole 133. For this reason, the light emitted from the first to third light emitting elements 121 to 123 can be partitioned using a simple configuration by machining a pre-existing holder 13 without separately providing an additional partitioning portion.

As shown in FIG. 4, in the holder 13, the plate thickness in portions close to the first to third holes 131 to 133 is greater than the dimension (thickness) relative to the Z direction of the first to third light emitting elements 121 to 123. The dimension in the direction orthogonal to the Z direction, or in other words, in the XY direction of the first to third holes 131 to 133 increases toward the +Z direction. Because of this, the range of light emitted from the first to third light emitting elements 121 to 123 is wider compared to the case where the dimension in the XY direction of the first to third holes 131 to 133 is constant with respect to the Z direction. Accordingly, the light emitted from the first to third light emitting elements 121 to 123 is more easily seen by the measurement subject.

A sheet-shaped light diffusion sheet 14 that covers the first to third holes 131 to 133 of the holder 13 is interposed between the holder 13 and the liquid crystal display element 115. Light that has been emitted from the first to third light emitting elements 121 to 123 in the +Z direction passes through the first to third holes 131 to 133 and is diffused through the light diffusion sheet 14. The diffused light passes through the cutout portion 110, furthermore passes through the lower glass 113 and the upper glass 114 of the liquid crystal display element 115 and the second polarizing plate 116, is emitted from the external face 10a of the main body, and is seen by the measurement subject or the like. Accordingly, the illumination range of the light emitted from the first to third light emitting elements 121 to 123 can be increased and light emission irregularities can be removed using the light diffusion sheet 141, which makes the emitted light easier for the measurement subject or the like to see.

Thus, in the blood pressure meter 1, the cutout portion 110 is provided in the region of the reflecting plate 111 and the first polarizing plate 112 of the display unit 11 that corresponds to the first to third light emitting elements 121 to 123.

Also, light that has been emitted from the first to third light emitting elements 121 to 123 passes through the cutout portion 110, furthermore passes through the liquid crystal display element 115 and the second polarizing plate 116 and is emitted from the external face 10a of the main body. For this reason, since the first to third light emitting elements 121 to 123 can be arranged so as to overlap with the display unit 11 along the XY plane, the area of the main body 10 with respect to the XY plane can be reduced and a reduction in the size of the blood pressure meter 1 can be realized. Also, light emitted from the first to third light emitting elements 121 to 123 that has passed through the cutout portion 110 and furthermore through the liquid crystal display element 115 and the second polarizing plate 116 is clearer than emitted light that has passed through a semi-transmissive type of liquid crystal panel, for example.

As shown in FIG. 4, an angle sensor 40 serving as an angle detection unit for detecting the angle of the wrist with respect to a pre-determined reference direction is provided on the substrate 15 in addition to the first to third light emitting elements 121 to 123. Also, a CPU (Central Processing Unit) and a control unit 50 including auxiliary circuits of the CPU are provided on the substrate 15. The control unit 50 performs control for causing the first to third light emitting elements 121 to 123 to emit light based on the angle detected by the angle sensor 40.

Figure 6A:
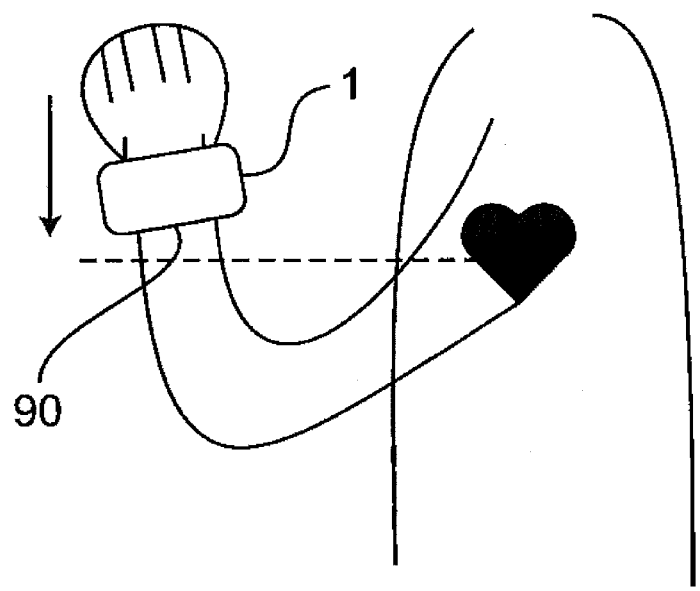
FIG. 6A is a diagram illustrating a state in which the position of the blood pressure meter is higher than the position of the heart of the measurement subject.
Figure 6B:
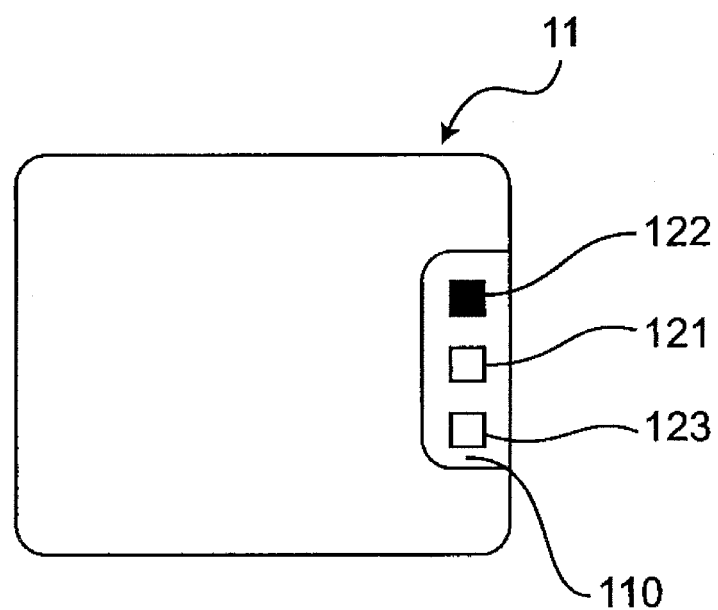
FIG. 6B is a diagram illustrating an example of display on the blood pressure meter when the position of the blood pressure meter is higher than the position of the heart of the measurement subject.

Operations and a usage method of the blood pressure meter 1 will be described next. The mode of using the blood pressure meter 1 and the display of the blood pressure meter 1 are illustrated in FIGS. 6A to 6C.

In order to obtain an accurate measurement value for blood pressure using the blood pressure meter 1, measurement needs to be performed while the position of the wrist to which the blood pressure meter 1 is attached is at the same height as the heart of the measurement subject. In this embodiment, first, the blood pressure meter 1 is attached to the left wrist 90, which is raised to the height of the heart, and in this state, the measurement subject starts blood pressure measurement by pressing a measurement start operation unit (not shown) provided on the external face 10a of the main body 10. At this time, the control unit 50 determines the reference direction based on the angle of the left wrist 90 detected by the angle sensor 40.

Next, the control unit 50 acquires orientation information for the measurement subject based on the angle of the left wrist 90 detected by the angle sensor 40. The orientation information indicates whether the detected angle of the left wrist 90 is larger than, smaller than, or within a pre-determined allowable range (e.g., ±5°) with respect to the reference direction.

Also, the control unit 50 functions as a light emission control unit so as to cause one of the first to third light emitting elements 121 to 123 to emit light based on the orientation information.

Specifically, as shown in FIG. 6A, when the detected angle of the left wrist 90 is larger than the allowable range and the left wrist 90 is at a higher position than the heart, the second light emitting element 122 emits light in the orange color, as shown in FIG. 6B. Thus it is possible to display the fact that the left wrist 90 is at a higher position than the heart to the measurement subject and to prompt the measurement subject to lower the position of the left wrist 90.

Figure 7A:
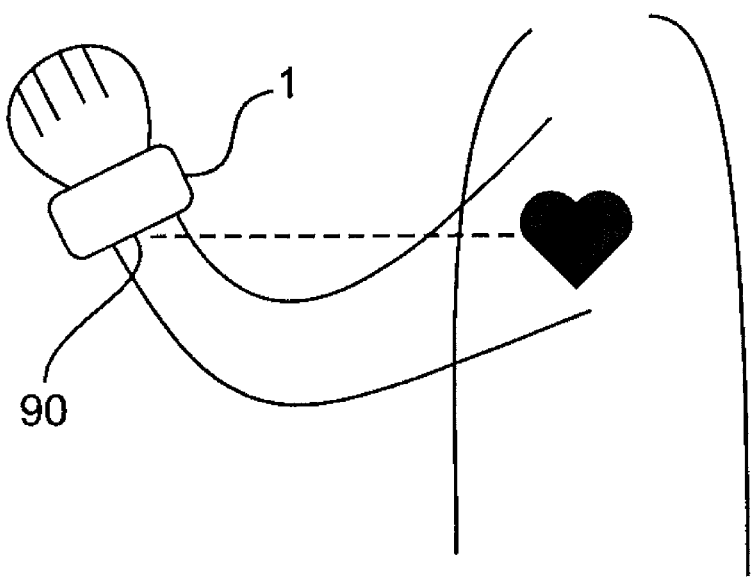
FIG. 7A is a diagram illustrating a state in which the position of the blood pressure meter is at almost the same height position as the heart of the measurement subject.
Figure 7B:
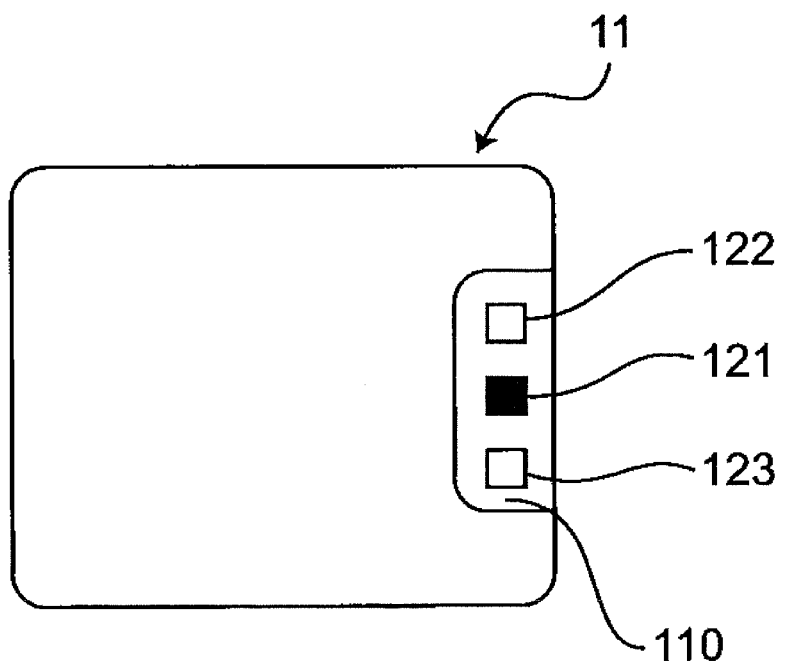
FIG. 7B is a diagram illustrating an example of display on the blood pressure meter when the position of the blood pressure meter is at almost the same height position as the heart of the measurement subject.

Also, when the detected angle of the left wrist 90 is within the allowable range and the height of the left wrist 90 is approximately the same as the height of the heart as shown in FIG. 7A, the first light emitting element 121 emits light in the blue color as shown in FIG. 7B. Thus, it is possible to display the fact that the height of the left wrist 90 is approximately the same as the height of the heart to the measurement subject and to cause the measurement subject to be careful to maintain the position of the left wrist 90.

Figure 8A:
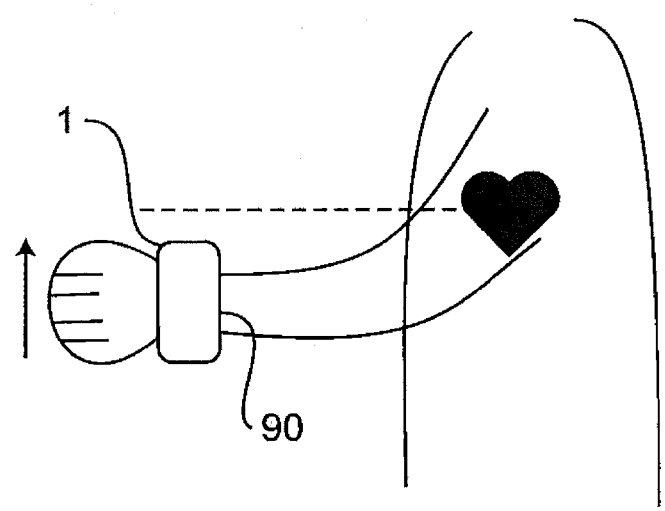
FIG. 8A is a diagram illustrating a state in which the position of the blood pressure meter is lower than the position of the heart of the measurement subject.
Figure 8B:
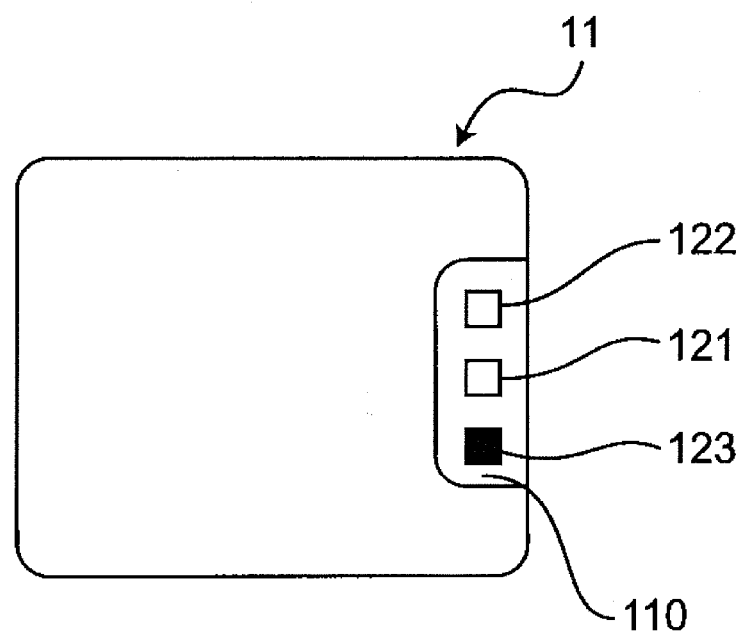
FIG. 8B is a diagram illustrating an example of display on the blood pressure meter when the position of the blood pressure meter is lower than the position of the heart of the measurement subject.

Also, as shown in FIG. 8A, when the detected angle of the left wrist 90 is smaller than the allowable range and the left wrist 90 is at a lower position than the heart, the third light emitting element 123 emits light in the orange color, as shown in FIG. 8B. Thus it is possible to display the fact that the left wrist 90 is at a lower position than the heart to the measurement subject and to prompt the measurement subject to raise the position of the left wrist 90.

In this way, with the blood pressure meter 1, the first to third light emitting elements 121 to 123 are caused to emit light based on the angle detected by the angle detection unit. Because of this, it is possible to clearly indicate the angle of the measurement site at the time of blood pressure measurement, or in other words, the orientation information of the measurement subject using the first to third light emitting elements 121 to 123. Accordingly, the measurement subject can measure his or her blood pressure at the correct orientation based on the orientation information, and a reduction in the size of the blood pressure meter 1 can be achieved without reducing usability.

Also, it is possible to indicate the orientation information of the measurement subject more clearly according to which of the first to second light emitting elements 121 to 123 is emitting light. Accordingly, the measurement subject can accurately measure his or her blood pressure at the correct orientation based on the orientation information.

Also, the color of light emitted by the first light emitting element 121 and the color of light emitted by the second and third light emitting elements 122 and 123 are different. That is to say, the color of light emitted by the first light emitting element 121 is blue, whereas the color of light emitted by the second and third light emitting elements 122 and 123 is orange. In human psychology, blue is easy to intuitively understand as signifying something that is accepted and permitted, and orange is easy to intuitively understand as signifying something that is prohibited. For this reason, it is possible to indicate the orientation information of the measurement subject more clearly according to the first to second light emitting elements 121 to 123. Accordingly, the measurement subject can measure his or her blood pressure with greater accuracy at the correct orientation based on the orientation information.

Also, the light emitted from the first to third light emitting elements 121 to 123 is partitioned by the first and second partition portions 141 and 142, and therefore it is easier for the measurement subject to see which of the light emitting elements is emitting light. Accordingly, the orientation information of the measurement subject can be indicated more clearly, and the measurement subject can measure his or her blood pressure with greater accuracy at the correct orientation based on the orientation information.

Note that although the blood pressure meter 1 was attached to the left wrist 90, it may be attached at any location on the human main body, such as the right wrist, an ankle, a finger, or the like.

Also, in the above-described embodiment, light that was emitted from the first to third light emitting elements 121 to 123 in the +Z direction passed through the first to third holes 131 to 133, but there is no limitation to this. For example, light that has been emitted from a light emitting element in the −X direction may be reflected in the +Z direction by a mirror (not shown), thus causing the reflected light to pass through a hole serving as a light emission path.

Also, in the above-described embodiment, the holder 13 included the first to third holes 131 to 133, but there is no limitation to this. For example, it is possible to include a U-shaped cutout portion instead of holes and partition the light emitted from the light emitting elements by separately providing partition portions.

Also, in the above-described embodiment, the first to third light emitting elements 121 to 123 were arranged on the substrate 15, but they may be arranged at any location, such as a side or the bottom of the main body.

Also, in the above-described embodiment, the light emitting unit included the first to third light emitting elements 121 to 123, but there is no limitation to this. One light emitting element may be provided, and the orientation information of the measurement subject may be indicated by a blinking pattern of the light emitting element. Also, it is possible to provide four or more light emitting elements so as to indicate the orientation information of the measurement subject.

Also, in the above embodiment, the first to third light emitting elements 121 to 123 are arranged in a row in the direction from the lower arm portion to the hand portion in the following order: the third light emitting element 123, the first light emitting element 121, and the second light emitting element 122, but there is no limitation to this. The light emitting elements may be arranged in any manner, as long as the measurement subject can understand when each of the light emitting elements emits light and the orientation information of the measurement subject can be indicated clearly.

Also, in the above embodiment, the color of light emitted by the first light emitting element 121 was blue, and the color of light emitted by the second and third light emitting elements 122 and 123 was orange, but it is possible for the color of light emitted by the first to third light emitting elements to all be the same color.

Also, in the above embodiment, the color of light emitted by the first light emitting element 121 was blue, and the color of light emitted by the second and third light emitting elements 122 and 123 was orange, but it is possible to use any combination of colors of emitted light, such as a combination of red and yellow, as long as the color of light emitted by the first light emitting element and the color of light emitted by the second and third light emitting elements are different.

REFERENCE SIGNS LIST

1 Blood pressure meter
10 Main body
10a External face
11 Display unit
13 Holder
20 Cuff
40 Angle sensor
50 Control unit
110 Cutout portion
111 Reflecting plate
112 First polarizing plate
115 Liquid crystal display element
116 Second polarizing plate
121 First light emitting element
122 Second light emitting element
123 Third light emitting element
131 First hole
132 Second hole
133 Third hole
141 First partition portion
142 Second partition portion

The invention claimed is:

1. A blood pressure meter comprising:
a blood pressure measurement cuff configured to be wrapped around a measurement site;
a main body attached to the blood pressure measurement cuff;
a display unit arranged extending along an external face of the main body on the side opposite to the blood pressure measurement cuff and configured to display first information related to the blood pressure of a measurement subject;
a light emitting unit arranged inside of the main body at a position that is farther from the external face than the display unit is; and
a control unit that is configured to and programmed to control the light emitting unit to emit light carrying second information that is different from the first information, wherein the display unit comprises a reflecting plate, a first polarizing plate, a liquid crystal display element, and a second polarizing plate in the stated order in a first direction from the inside to the external face of the main body, wherein the light emitting unit is positioned in an overlapped manner with the liquid crystal display element when viewed in the first direction,
wherein the light emitted from the light emitting unit is viewable within a display area of the display unit defined by the liquid crystal display element, and wherein regions of the reflecting plate and the first polarizing plate that correspond to the light emitting unit are cut out such that light from the light emitting unit is emitted through the liquid crystal display element and the second polarizing plate along the first direction.

2. The blood pressure meter according to claim 1, wherein the main body comprises:
an angle detection unit configured to detect an angle of the measurement site with respect to a pre-determined reference angle; and
a light emission control unit configured to perform control for causing the light emitting unit to emit light based on the angle detected by the angle detection unit.

3. The blood pressure meter according to claim 2,
wherein the light emitting unit includes three light emitting elements arranged in a row along a width direction of the blood pressure measurement cuff, and
wherein the light emission control unit causes a first light emitting element arranged in the center of the three light emitting elements to emit light when the detected angle is within a pre-determined range, the light emission control unit causes a second light emitting element arranged on one side of the three light emitting elements to emit light when the detected angle is larger than a pre-determined range, and the light emission control unit causes a third light emitting element arranged on the other side of the three light emitting elements to emit light when the detected angle is smaller than a pre-determined range.

4. The blood pressure meter according to claim 3, wherein a color of light emitted by the first light emitting element and a color of light emitted by the second and third light emitting elements are different.

5. The blood pressure meter according to claim 3, wherein the main body includes a partition portion that partitions light emitted by the three light emitting elements respectively.

6. The blood pressure meter according to claim 5,
wherein between the reflecting plate and the three light emitting elements, the main body includes a holder having a planar dimension that is substantially the same as the planar dimension of the liquid crystal display element, wherein in regions that correspond to the three light emitting elements with respect to a direction orthogonal to the first direction, the holder includes a light emission path that allows light from the light emitting element to pass in the first direction, and wherein the partition portions are formed in regions of the holder that are between adjacent light emission paths.

7. The blood pressure meter according to claim 6, wherein the holder has a thickness that exceeds the dimension of the light emitting element with respect to the first direction, and wherein the dimension in a direction orthogonal to the first direction of the light emission path increases in the first direction.

8. The blood pressure meter according to claim 4, wherein the main body includes a partition portion that partitions light emitted by the three light emitting elements respectively.

* * * * *